United States Patent
Damaj

(10) Patent No.: US 7,541,054 B2
(45) Date of Patent: Jun. 2, 2009

(54) METHODS OF EXTRACTING AN ANTI-MICROBIAL FRACTION FROM JUGLANS REGIA

(75) Inventor: Bassam B. Damaj, San Diego, CA (US)

(73) Assignee: Bio-Quant, Inc., San Diego, CA (US)

( * ) Notice: Subject to any disclaimer, the term of this patent is extended or adjusted under 35 U.S.C. 154(b) by 0 days.

(21) Appl. No.: 11/197,909

(22) Filed: Aug. 5, 2005

(65) Prior Publication Data

US 2006/0034956 A1   Feb. 16, 2006

Related U.S. Application Data

(60) Provisional application No. 60/599,541, filed on Aug. 6, 2004.

(51) Int. Cl.
| | |
|---|---|
| A01N 65/00 | (2006.01) |
| A61K 36/00 | (2006.01) |
| A61K 36/20 | (2006.01) |
| A61K 36/40 | (2006.01) |
| A61K 36/44 | (2006.01) |
| A61K 36/49 | (2006.01) |
| A61K 36/52 | (2006.01) |
| A61K 36/63 | (2006.01) |
| A61K 36/76 | (2006.01) |

(52) U.S. Cl. .................. 424/771; 424/773; 424/775
(58) Field of Classification Search .................. None
See application file for complete search history.

(56) References Cited

U.S. PATENT DOCUMENTS

| 5,137,717 A | 8/1992 | Wixforth |
| 6,264,926 B1 | 7/2001 | Farooqi et al. |
| 6,395,261 B1 | 5/2002 | Laforet |
| 2003/0068358 A1 | 4/2003 | Frater-Schroder et al. |

FOREIGN PATENT DOCUMENTS

EP    1 323 354 A2   7/2003

OTHER PUBLICATIONS

Mouhajir F., Pedersen J.A., Rejdali M., Towers G.H.N. Pharmaceutical Biology. 2001; 39(5): 391-398.*
Erdemoglu N., Kupeli E., Yesilada E. J. Ethanopharm. 2003; 89: 123-129.*
http://s148978007.oneandoneshop.com/html/body_whatisturkishwalnut.html.*
Fukuda T., Ito H., Yoshida T. Phytochemistry. 2003; 63: 795-801.*
Keith E.S., Powers J.J. Applied Microbiology. 1965; 13(3): 308-313.*
Ali-Shtayeh M.S., Abu Ghdeib S. I. Mycoses. 1999; 42: 665-672.*
Mouhajir F., Hudson J.B., Rejdali M., Towers G.H.N. Pharmaceutical Biology. 2001; 39(5): 364-374.*
Ahmad S., Wahid M.A., Bukhari A.Q.S. Antimicrobial Agents and Chemotherapy 1973; 3(3): 436-438.*
Mouhajir F., Pedersen J. A.. Rejdali M., Towers G.H.N. Pharm. Bio. 2001; 39(5): 391-398.*
Mouhajir F., Hudson J.B., Rejdali M. Towers G.H.N. Pharmaceutical Biology. 2001; 39(5): 364-374.*
Solvent Wastes in the Laboratory—Disposal and/or Recycling.*
Green, J. The Herbal Medicine-Makers Handbook: A Home Manual. Berkeley, The Crossing Press, 2000, pp. 146-152 and 154.*
Fukuda et al. Phytochemistry. 2003; 63: 795-801.*
Keith et al. Applied Microbiol. 1965; 13(3): 308-313.*
"Walnut: Botanical and Common Names," http://www.innvista.com/HEALTH/herbs/walnut.htm [online] [retrieved on May 19, 2004].
"Plants: Pacific Northwest," http://www.ernestartist.org/JuglansRegia01.htm [online] [retrieved on May 19, 2004].
"American Botanical Council's Herb-Ed-Web," http://www.herbalgram.org/iherb/expandedcommissione/hel100.asp [online] [retrieved on May 19, 2004].
Onken, Michael, "Re: Looking for any medical research that involves any part of a walnut tree," http://www.madsci.org/posts/archives/may98/893971900.Me.r.html [online] [retrieved on Jul. 29, 2005].
"Anti-Cancer Drug Plants," http://www.ghmpix.com/gardens/anti_cancer.htm [online] [retrieved on May 19, 2004].
"Cancer Treatment Products," http://www.expage.com/cancercure [online] [retrieved on May 19, 2004].
Ryo et al., "Prolyl isomerase Pin 1: a catalyst for oncogenesis and a potential therapeutic target in cancer," Journal of Cell Science, 2003, pp. 773-783, vol. 116.
Rippmann et al., "Phosphorylation-dependent Proline Isomerization Catalyzed by Pin1 Is Essential for Tumor Cell Survival and Entry Into Mitosis," Cell Growth and Differentiation, Jul. 2000, pp. 409-416, vol. 11.
Ali-Shtayeh et al., "Antifungal activity of plant extracts against dermatophytes," Mycoses, 1999, pp. 665-672, vol. 42.
Cai et al., "Nambian chewing stick, Diospyros lyciodes, contains antibacterial compounds against oral pathogens," J. Agric Food Chem, Mar. 2000, pp. 909-914, vol. 48.
Alkhawajah, Abdulaziz M., "Studies on the Antimicrobial activity of *Juglans regia*," The American Journal of Chinese Medicine, 1997, pp. 175-180, vol. 25, No. 2. Abstract.
Mouhajir et al., "Phenolics in Moroccan Medicinal Plant Species as Studied by Electron Spin Resonance Spectroscopy," Pharmaceutical Biology, 2001, pp. 391-398, Vo. 39, No. 5.

* cited by examiner

Primary Examiner—Christopher R. Tate
Assistant Examiner—Amy L Clark
(74) Attorney, Agent, or Firm—TraskBritt

(57) ABSTRACT

A biologically active composition which has desirable properties, for example, anti-microbial and anti-cancer properties is disclosed. A process for preparing active ingredient(s) of the composition of the present invention, including, for example, extraction of the active ingredient(s) from a natural product is also disclosed. The biologically active composition may be extracted from a part of a variety of the walnut species *J. regia* L.

12 Claims, 5 Drawing Sheets

METHODS OF EXTRACTING AN ANTI-MICROBIAL FRACTION FROM *JUGLANS REGIA*

PRIORITY CLAIM

Pursuant to the provisions of 35 U.S.C. § 119(e), this application claims the benefit of the filing date of Provisional Patent Application Ser. No. 60/599,541, filed Aug. 6, 2004, for "Biologically Active Composition."

TECHNICAL FIELD

This invention relates to a biologically active composition which has desirable properties, for example, anti-microbial and anti-cancer properties. This invention relates also to a process for preparing active ingredient(s) of the composition of the present invention, including, for example, extraction of the active ingredient(s) from a natural product.

BACKGROUND

Healthcare products that contain one or more biologically active compounds which appear in nature are well known. The present invention relates to one or more biologically active compounds which can be derived from a part (for example, the root) of a variety (cultivar) of a species of the genus *Juglans* L., which is a member of the plant family known as Juglandaceae (also referred to as the "walnut family"). The genus *Juglans* L. contains over ten species, including, for example, *Juglans ailanthifolia* Carr. (Japanese walnut P), *Juglans boliviana* (C. DC.), Dode (Bolivian walnut P), *Juglans californica* S. Wats. (Southern California walnut P), *Juglans cinerea* L. (butternut P), and *Juglans neotropica* Diels (Andean walnut P).

Another of the species of the genus *Juglans* L. is *Juglans regia* L., referred to herein as "*J. regia* L." There are numerous varieties of walnut trees which are members of the species *J. regia* L., for example, walnut trees grown in various geographical areas throughout the world, including, for example, in North and South America, Asia, Europe, and Africa. A source of the biologically active material of the present invention includes parts of selected varieties, as described below, of the walnut species *J. regia* L.

SUMMARY OF THE INVENTION

In accordance with the present invention, there is provided a process for extracting from a part of a variety of the walnut species *J. regia* L. a biologically active extract comprising treating the part with an aqueous solvent under extracting conditions and for a sufficient period of time to extract from the part an aqueous solution which contains in dissolved form the extract, wherein the variety of *J. regia* L. is selected from the group consisting of walnut trees grown in Morocco, Spain, Turkey, Afghanistan, Southern Russia, India, China, Greece, Chile, Iran, Japan, Tunisia, Algeria, France, Portugal, Southeast Asia, Bangladesh, Bahrain, Iraq, Israel, Jordan, Kuwait, Lebanon, Oman, Qatar, Syria, United Arab Emirates (UAE), Yemen, Cyprus, Armenia, Azerbaijan, Georgia, Libya, Egypt, Sudan, Mauritania, Mali, Niger, Nigeria, Chad, and Ethiopia, or such trees grown in other geographical areas. The term "biologically active extract" means an extract in which any part thereof has one or more of a physiological, chemical, pharmacological, or biological effect on the whole of an organism or on a specific part of an organism or cell.

The aqueous solvent used to extract the biologically active extract comprises a major amount of water, as described hereinafter.

In preferred form, the biologically active extract is derived from a part of the Moroccan walnut tree, preferably the bark or root thereof.

Another aspect of the present invention is the provision of a biologically active composition which contains an effective amount of one or more compounds present in the aforementioned biologically active extract, including, for example, compositions which are capable of functioning as anti-microbial agents or anti-fungal agents or anti-cancer agents. One exemplary form of the composition that it is believed will be used widely is a mouthwash which contains the biologically active extract, particularly a non-alcoholic mouthwash.

BRIEF DESCRIPTION OF THE DRAWINGS

The following are drawings which are illustrative of embodiments of the invention and drawings which contain comparative information.

DETAILED DESCRIPTION OF THE INVENTION

Figure 1:
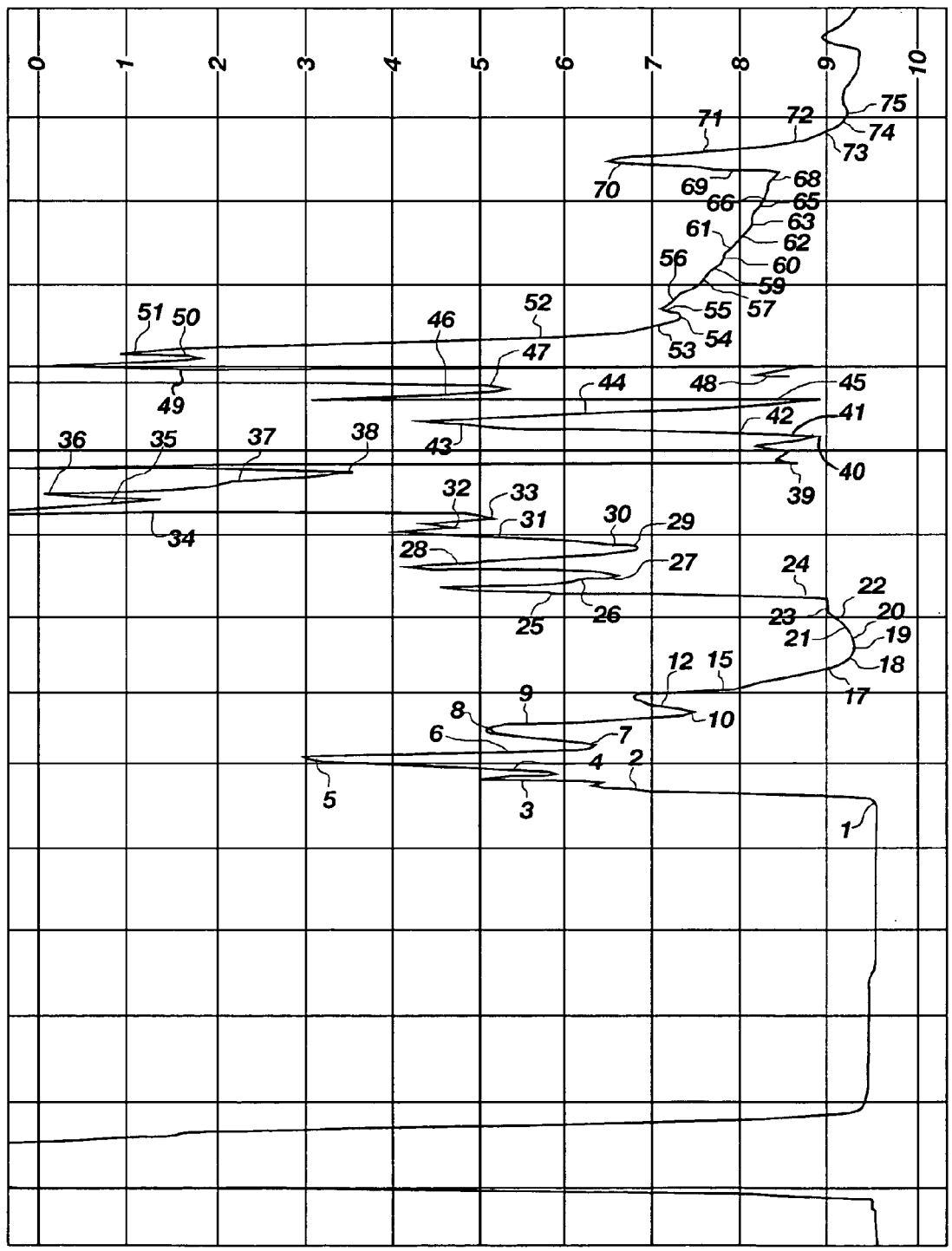
FIG. 1 depicts a high-pressure liquid chromatography (hereafter "HPLC") tracing of a biologically active extract prepared in accordance with the present invention from the root of a Moroccan walnut tree.

A source of the biologically active extract of the present invention comprises one or more tree parts of selected varieties of the walnut species *J. regia* L. Although there are other varieties of walnut trees of the species *J. regia* L., examples of varieties of the *J. regia* L. for use in the present invention are walnut trees which are grown in the following countries or regions: Morocco, Spain, Turkey, Afghanistan, Southern Russia, India, China, Greece, Chile, Iran, Japan, Tunisia, Algeria, France, Portugal, Southeast Asia, Bangladesh, Bahrain, Iraq, Israel, Jordan, Kuwait, Lebanon, Oman, Qatar, Syria, United Arab Emirates (UAE), Yemen, Cyprus, Armenia, Azerbaijan, Georgia, Libya, Egypt, Sudan, Mauritania, Mali, Niger, Nigeria, Chad, and Ethiopia, or such trees grown in other geographical areas. The walnut species *J. regia* L. is known also as the "English" walnut, the "Carpathian" walnut and as the "Persian" walnut.

A preferred source of the biologically active material for use in the composition of the present invention is a part of the Moroccan walnut tree, which includes cultivated walnut trees that cover an area of about 7600 Ha in Morocco. It has been reported that more than half of the plantings are seedlings resulting from the prevailing way of seed propagation known by farmers. Trees are cultivated in mountainous and remote areas between 800 and 1800 m above sea level and under different environments which include cultivated walnut trees that have resulted in the presence of genetic variability. Using Principal Component Analysis on a total of 39 nut, kernel and vegetative traits in Morocco, 55 Moroccan walnut seedlings and seven French varieties and selections have been studied. The results show that the existing genetic variability is manifested by shoot length and diameter, nut size, and kernel and shell weights. Genotypes from Northern Morocco (Rif Mountains) seem to represent a separate ecotype characterized by a lateral fruiting habit and small fruits. Moroccan germplasm showed smaller fruits, more shriveled kernels, higher aborted buds, and lower fruiting potential as compared to French germplasm.

Bark from Moroccan walnut trees is sweet and does not share the acrid bitter taste and/or smell of other walnut varieties; these are distinguishing characteristics of the Moroccan walnut tree.

The preferred walnut tree parts for use in the present invention are the roots and bark of the trees, most preferably the roots of the trees. As described in detail below, the parts are converted preferably to a powder by crushing or grinding prior to being treated with the aqueous solvent to extract therefrom the active ingredients.

Any suitable method involving the use of the aqueous solvent of the present invention can be used to extract the water-soluble biologically active ingredients from the parts of the aforementioned walnut trees. The extracting conditions should be carried out for a period of time sufficient to produce a liquid extract that contains about 20 wt. % of dissolved biologically active extract in the aqueous solvent. (Unless stated otherwise, "wt. %," as used herein, means percent by weight based on the total weight of the composition.) Preferably, the biologically active extract comprises about 20 wt. % of the aqueous solution, for example, 20 kg of the dissolved extract in 100 L of aqueous solution.

Any suitable form of the part of the walnut tree can be used in the extraction, for example, chunks of the part. In preferred form, the part of the walnut tree is dried and reduced to a powder, for example, by a grinding or pulverizing operation which involves subjecting the roots or bark of the walnut tree to grinding or crushing to particles which can vary in size over a relatively wide range. Preferably, a powder of fine particles is used and the powder is macerated with the aqueous solvent.

The aqueous solvent for use in the extraction comprises at least about 70 wt. % water, preferably at least about 90 wt. % water, most preferably about 100 wt. % water. As the concentration of water comprising the aqueous solvent is reduced, the biological effectiveness of the extract which is obtained from treatment with lower amounts of water in the aqueous solvent is reduced.

It should be appreciated that the aqueous solvent that is used to prepare the biologically active extract of the present invention is significantly different from saliva which is a unique composition. For example, saliva is a relatively viscous material which contains enzymes and has a pH which averages about 6 to about 6.5. Water, for example, deionized water, has a pH which averages about 4.5 to about 5, has a lower viscosity than saliva, and does not contain enzymes present in saliva.

An aqueous solvent which comprises less than about 100 percent water can include a material which functions as a co-solvent. An example of such a material is an alcohol such as, for example, ethanol or methanol.

The extraction should be conducted under temperature conditions which reduce the tendency of the biologically active ingredients comprising the extract to decompose. It is recommended that the temperature of the aqueous solvent be no greater than about 60° C. and preferably in the range of about 4° C. to about 20° C. When the aqueous solvent has a temperature other than ambient or room temperature (about 23° C.), refrigerating or heating equipment can be used to lower or raise the temperature of the solvent to the desired operating temperature.

The extracting conditions which involve contacting the parts of the walnut tree with the aqueous solvent at the desired temperature should be carried out for a period of time sufficient to produce an aqueous solution which has the desired concentration of dissolved biologically active extract, for example, about 20 wt. %. Inasmuch as the water-soluble biologically active materials which comprise the extract are present in the walnut tree part in very small amounts, for example, less than about 10 wt. %, relatively large quantities of aqueous solvent and relatively long periods of time are needed to arrive at the desired concentration of extract in the concentrated aqueous solution that is produced by the extraction. For example, in treating the roots of a Moroccan walnut tree, about 1000 kg of the roots can be treated over a period of about 100 days with an aqueous solvent that comprises substantially all water at a temperature of about 4° C. to produce a concentrated aqueous solution of extract that comprises about 20 wt. % of biologically active extract.

A recommended process for providing the concentrated aqueous solution of extract involves a multi-step process in which a powder of the walnut tree part is mixed with the aqueous solvent for a prolonged period of time (for example, one to two days) after which the resulting aqueous solution (hereafter "solution 1") is separated from the powder (hereafter the "powder residue") with pressing. The powder residue which contains "left-over" water-soluble active ingredients is contacted with additional aqueous solvent for a prolonged period of time (for example, one to two days) with stirring, after which the aqueous solvent is separated from the residue powder with pressing and the resulting aqueous solution containing dissolved biologically active ingredients is added to aforementioned "solution l" along with an additional amount of powder of the walnut tree part. These various steps can be repeated until the desired amount of biologically active extract is obtained. The extract in a solid powder form can be recovered from the solution by evaporating the liquid solvent. Prior to evaporation, the solution can be filtered, as may be needed, to remove therefrom solid impurities.

The invention includes within its scope the use of compounds comprising the biologically active extract, including compounds comprising the anti-microbial fraction of the extract, and synthetic forms of such compounds, that is, such compounds prepared by appropriate synthesis.

Example No. 1 below describes a preferred process for preparing a preferred biologically active extract of the present invention. FIG. 1 is a HPLC tracing of the preferred extract. The tracing includes approximately 75 fractions which represent compounds contained within the extract. The extract which is the subject of the tracing of FIG. 1 can be used in an anti-cancer composition as described below.

The tracing of FIG. 1 includes also the identification of the anti-microbial fraction of the extract, as described below. The anti-microbial fraction can be separated from the extract by liquid chromatography as described in Example No. 2 below and can be used in anti-microbial compositions as described below.

As described in Example No. 1, the biologically active extract was derived from the roots of the Moroccan walnut tree. The HPLC procedure that was used to arrive at the "extract" tracing of FIG. 1 is described hereafter. A 4.9 ml sample of the 20 wt. % solution of the extract of Example No. 1 was diluted to 100 ml with distilled water. The chromatography was performed using a C18 column (Vydac C18

(218TP54), 4.6 x 250 mm). The column was equilibrated with 0.1% TFA-Water (v/v) (Buffer A) and the concentrate was eluted with 0.1% TFA-60% acetonitrile-water (v/v) (Buffer B) at 1.2 mL/minute at a gradient of 0% B for 10 minutes, 0-100% B in 100 minutes. The elution was monitored by absorbance at 254 nm, as the tracing of FIG. 1 was produced.

The 75 fractions shown in the tracing of FIG. 1 and in the form of liquid solutions were isolated, evaporated and weighed before analyzing for microbial activity. Samples of each of the fractions were resuspended in water to a normalized 1 mg/ml concentration. Out of the 75 fractions tested, 17 fractions showed some level of anti-microbial activity. Fractions Nos. 34 and 35 showed a strong (R=9 to 11 mm, for *E. coli*) inhibition, fraction No. 36 showed an intermediate strength (R=3 to 5 mm) inhibition, and fractions Nos. 1, 2, 26, 32, 37, 40, 46, 47, 49, 58, 59, 60, 67, and 70 showed a weak inhibition (R<3 mm). The aforementioned 17 fractions are referred to herein as the "anti-microbial fraction" of the extract of the present invention. Compounds comprising fraction Nos. 34, 35, and 36 are preferred for use in anti-microbial applications.

The anti-microbial fraction of the present invention can be used in formulating compositions which are effective in treating conditions that involve microbial infections. The microbial infection may be present in a human or other mammals or non-mammals. As evidenced in the Example section hereof, the anti-microbial fraction is effective in inhibiting the growth of a variety of bacterial strains. Examples of compositions in which the anti-microbial fraction can be used include mouthwashes, topical anti-bacterial applications, and any other conditions or diseases involving microbial infection which can be alleviated by use of the anti-microbial fraction hereof. Any suitable form of the composition can be used. Examples of such forms are an aqueous solution, a cream, soap, ointment, gel, hydrated powder, and a tablet. The composition can be administered in any suitable way, for example, by oral administration, by topical administration, such as by use of a patch or spray, or by any other mode of delivery system that presents the composition to the microbe in question. The anti-microbial composition comprises typically other ingredients, for example, stabilizers, surfactants, colorants, fragrances, and additional anti-microbials, or any ingredient needed to make a final desired and suitable formulation for the uses indicated above.

The anti-microbial fraction should be present in the composition in an amount effective to deter the growth of the microbe. The amount will depend generally on various factors, including, for example, the nature of the bacterial strain and its resistance, and the site of infection. It is believed that for most applications, the amount of the anti-microbial fraction will comprise from about 1 to about 100 wt. % of the composition, preferably from about 10 to about 20 wt. % of the composition.

It is believed that a popularly used form of the anti-microbial fraction of the present invention will be in oral rinse compositions, including mouthwashes, which are alcohol free or are substantially free of alcohol, that is, the concentration of alcohol is no greater than about 0.1 wt. %. An advantage associated with the use of such compositions is that they are considered to be healthier than alcohol-containing compositions.

As mentioned above, the biologically active extract which contains the anti-microbial fraction of the present invention can be used to treat fungal infections. The fungal infection may be present in a human or other mammals or non-mammals. Various types of fungal infections can be treated. Examples of common fungal infections that can be treated are those caused by: *Candida albicans*, *Malassezia furfur*, *Madurella mycetomatis*, *Paracoccidioides brasiliensis*, *Coccidioides immitis*, *Cryptococcus neoformans*, and *Aspergillus fumigatus*. The Examples section herein includes experimental data showing the effective treatment of *Candida albicans*.

Examples of compositions in which the biologically active extract can be used include mouthwashes, oral and vaginal anti-fungal rinses, topical anti-fungal applications, and any other conditions or diseases involving fungal infections which can be alleviated by use of the biologically active extract hereof. Any suitable form of the composition can be used. Examples of such forms are an aqueous solution, a cream, soap, ointment, gel, hydrated powder, and a tablet. The composition can be administered in any suitable way, for example, by oral administration, by topical administration, such as by use of a patch or spray, or by any other mode of delivery system that presents the composition to the fungus in question. The anti-fungal composition comprises typically other ingredients, for example, stabilizers, surfactants, colorants, fragrances, and additional anti-fungals, or any ingredient needed to make a final desired and suitable formulation for the uses indicated above.

The biologically active extract should be present in the composition in an amount effective to deter the growth of the fungus. The amount will depend generally on various factors, including, for example, the nature of the fungal strain and its resistance, and the site of infection. It is believed that for most applications, the amount of the biologically active extract will comprise from about 1 to about 100 wt. % of the composition.

As mentioned above, the biologically active extract which contains the anti-microbial fraction of the present invention can be used to treat cancer. The cancer may be present in a human or other mammals or non-mammals. Various types of cancers can be treated (see internet, www.nci.nih.gov, A to Z List of Cancers). Examples of common cancer types that can be treated are: bladder cancer; breast cancer; colon and rectal cancer; endometrial cancer; kidney cancer (renal cell); leukemia; lung cancer; melanoma; non-Hodgkin's lymphoma; prostate cancer; pancreatic cancer. The Examples section herein includes experimental data showing the effective treatment of breast cancer cells.

The extract is administered in an amount sufficient to deter the initial or continuing development of the cancer; it can be administered over a period of time sufficient to halt the growth of the cancer cells or to kill the cancer cells. As used herein, the term "sufficient amount" means an amount which is effective in inducing death or halting the growth of cancer cells. The extract should be administered according to a desired dosing regimen to provide the desired therapeutic activity. It should be appreciated that suitable dosage and dosing regimens will depend on various factors, including, for example, the particular cancer being treated, the severity of the condition, and the general health, age, and weight of the subject.

The extract may be administered in a single dose or a series of doses. Exemplary dosages lie within the range of about 1 mg/kg to about 1000 mg/kg of body weight per dosage.

Although the biologically active extract can be administered in neat form, it is administered preferably in the form of a pharmaceutical composition which contains one or more excipients of the type known to those skilled in the art. Any suitable forms of the composition may be used. Examples of such forms are an aqueous solution, pill, capsule, and a tablet. The composition may be administered by oral administration, or by any other mode of delivery system that presents the composition to the cancerous cells in question. The composition may contain any suitable carriers or diluents, for example, solvents, dispersion media, fillers, solid carriers, coatings, antifungal and antibacterial agents, dermal penetration agents, surfactants, isotonic and absorption agents and the like. It should be understood that the composition may include also other supplementary biologically active agents.

The biologically active extract can be included also in a food composition for administration to the subject. The food composition may be produced using various suitable food materials. Examples of food materials are rice, wheat, corn, potato, sweet potato, soybean flour, seaweed (sea tangle, wakame (*Undaria pinnatifida*), agar-agar, etc.) flour, starch syrup, lactose, glucose, fructose, sucrose, mannitol and the like. These materials may be used alone or in suitable combination with one another. The food composition may be made up into desired shape, if necessary, by adding water or the like. In addition, flavoring agents, coloring agents, sweetening agents, edible oils, vitamins and the like may be added suitably to the food composition.

Figure 2:
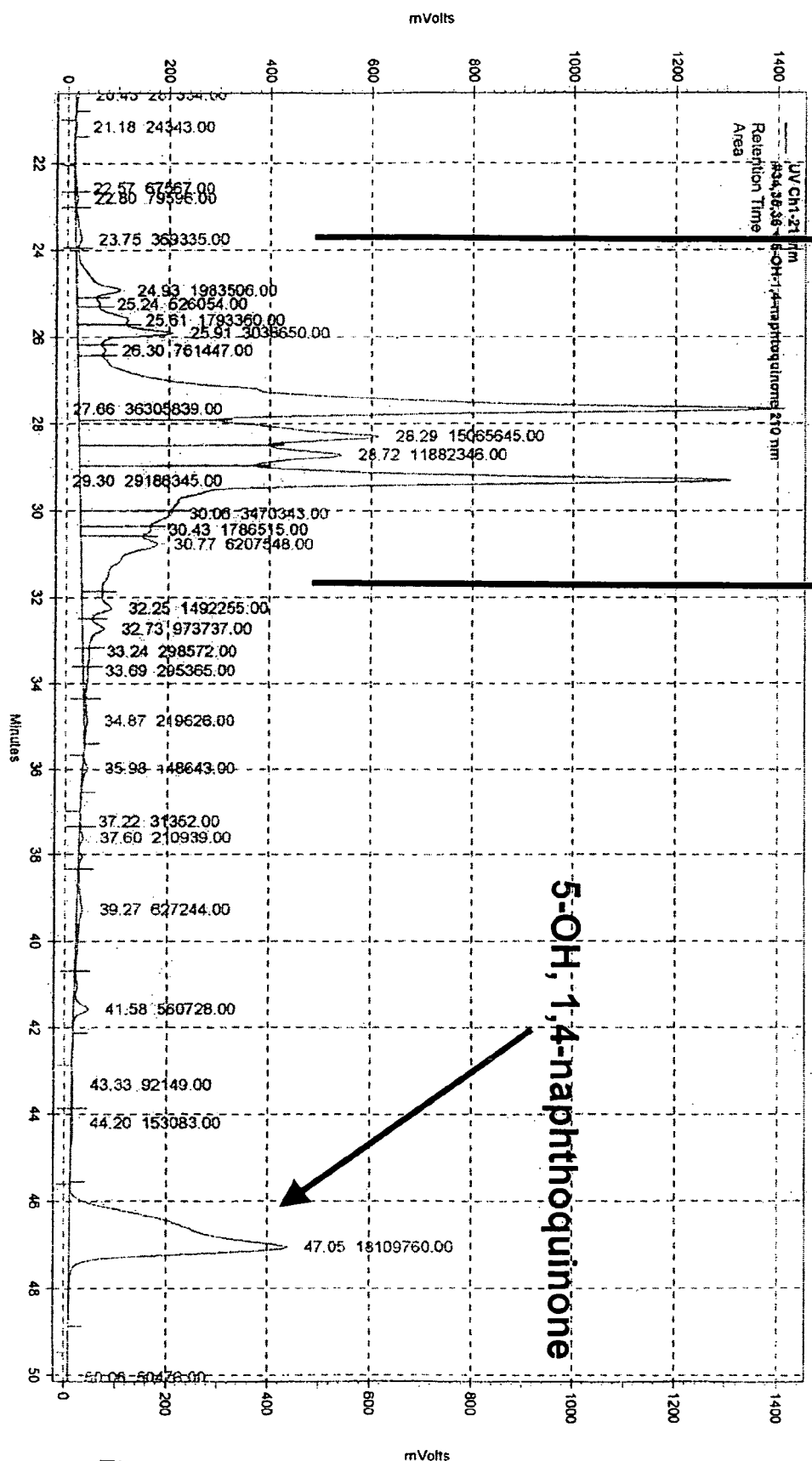
FIG. 2 depicts an HPLC tracing of a mixture of 5-hydroxy-1,4-naphthoquinone and a biologically active extract prepared in accordance with the present invention from the root of a Moroccan walnut tree.

FIG. 2 hereof contains information which shows that a prior art compound that is reported as having germicidal properties and as being derived from part of a walnut tree is not a compound that is contained within the anti-microbial fraction of the present invention. The prior art compound is 5-hydroxy,1,4-naphthoquinone (hereafter for convenience "the quinone") which is described in U.S. Pat. No. 5,137,717 to Wixforth as having germicidal properties and which is described for use in various types of anti-germicidal preparations, for example, a mouthwash. The Wixforth patent discloses that the quinone is present in an extract which is derived from a plant part (for example, the bark of a tree) which belongs to the family Juglandaceae and the genus *Juglans* L., for example, the species *J. regia* L. and *J. nigra* L. The Wixforth patent does not identify any variety of walnut tree belonging to the aforementioned species; the examples of the patent refer generally to the use of root or bark from *J. regia* L. to derive the quinone. The extraction used to derive the quinone is described in the patent as involving the use of an extracting agent comprising 70% to 100% of ethanol and 0% to 30% water.

FIG. 2 is an HPLC tracing of the anti-microbial fraction of the present invention as described in Example No. 1 below in admixture with the quinone. The chromatography was performed using a C18 column (Vydac C18 (218TP54), 4.6×250 mm). The column was equilibrated with 0.1% TFA-Water (v/v) (Buffer A) and the concentrate was eluted with 0.1. % TFA-60% acetonitrile-water (v/v) (Buffer B) at 1.2 mL/minute at a gradient of 0% B for 10 minutes, 0-100% B in 100 minutes. The elution was monitored by absorbance at 210 nm. The tracing shows that 5-hydroxy-1,4-naphthoquinone elutes under these conditions at 47.11 minutes and is not contained within the anti-microbial fraction of the present invention which elutes under these conditions at 23.5 to 31.5 minutes.

Figure 3:
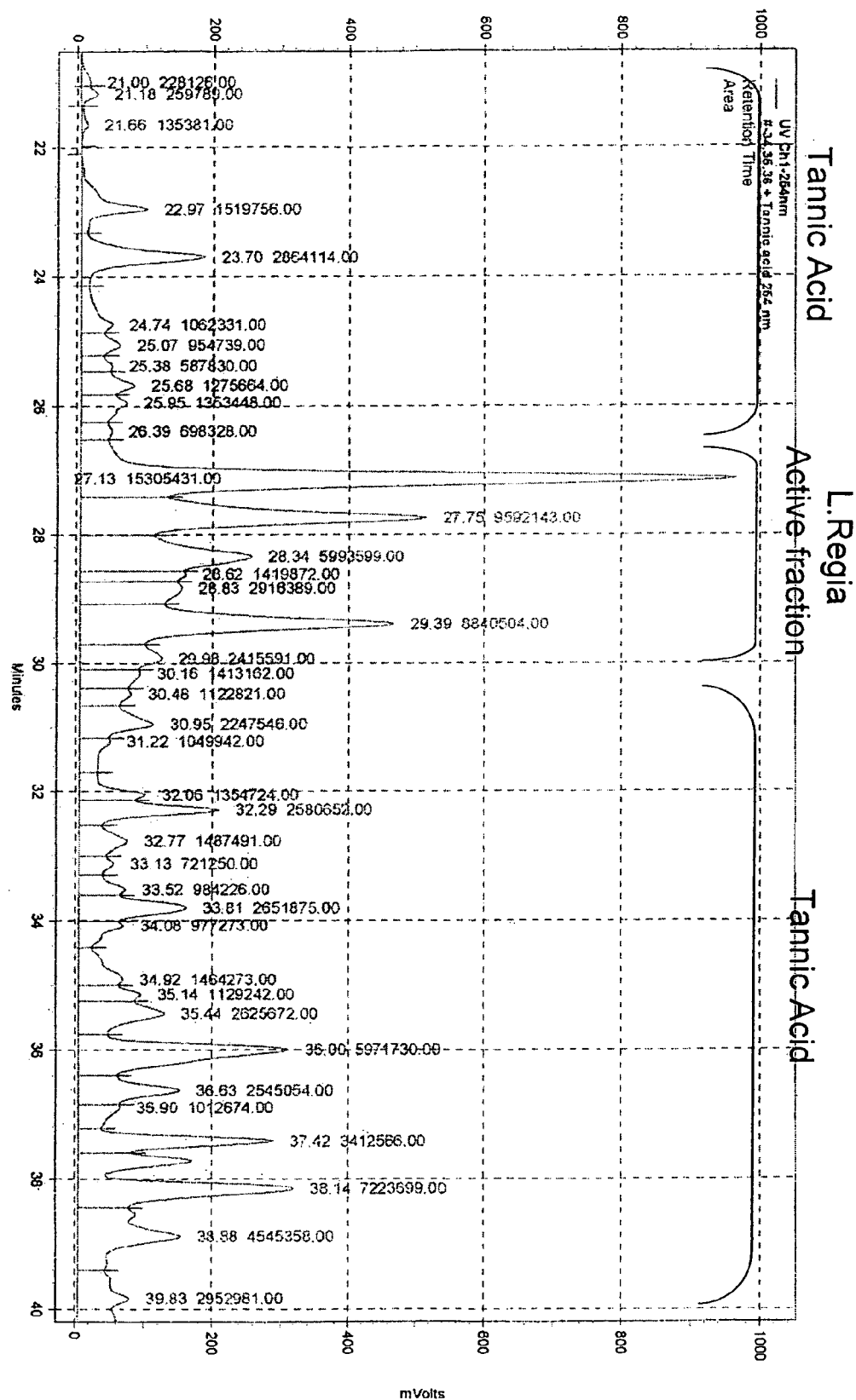
FIG. 3 depicts an HPLC tracing of a mixture of tannic acid and a biologically active extract prepared in accordance with the present invention from the root of a Moroccan walnut tree.

FIG. 3 hereof contains information which shows that a prior art extract which is capable of being derived by use of an aqueous solvent from the part of a walnut tree of the species *J. regia* L. is an extract that is different from the anti-microbial fraction of the present invention. The prior art extract comprises tannin which is described in published European patent application EP 1 323 354 as being capable of being extracted by use of an aqueous solvent from parts of a walnut tree belonging to the species *J. regia* L. The extract is described as having the ability to affect the composition of micro-organisms in the intestinal canal in monogastric animals. The European published application does not identify the variety of walnut tree that is the source of the extract.

FIG. 3 is an HPLC tracing of an anti-microbial fraction of the present invention as described in Example No. 1 below in an admixture with tannic acid. The information in the tracing was obtained by the use of a procedure which is similar to the procedure described above in connection with the tracing of FIG. 2, except that the elution was monitored by absorbance at 264 nm. The tannic acid was obtained from Sigma Aldrich (Missouri, USA), product No. T-0200 and was used without any purification. The tracing shows that tannic acid is composed of several fractions and that the active fractions of the biologically active extract of the present invention are not contained within the fractions of the tannic acid.

Figure 4:
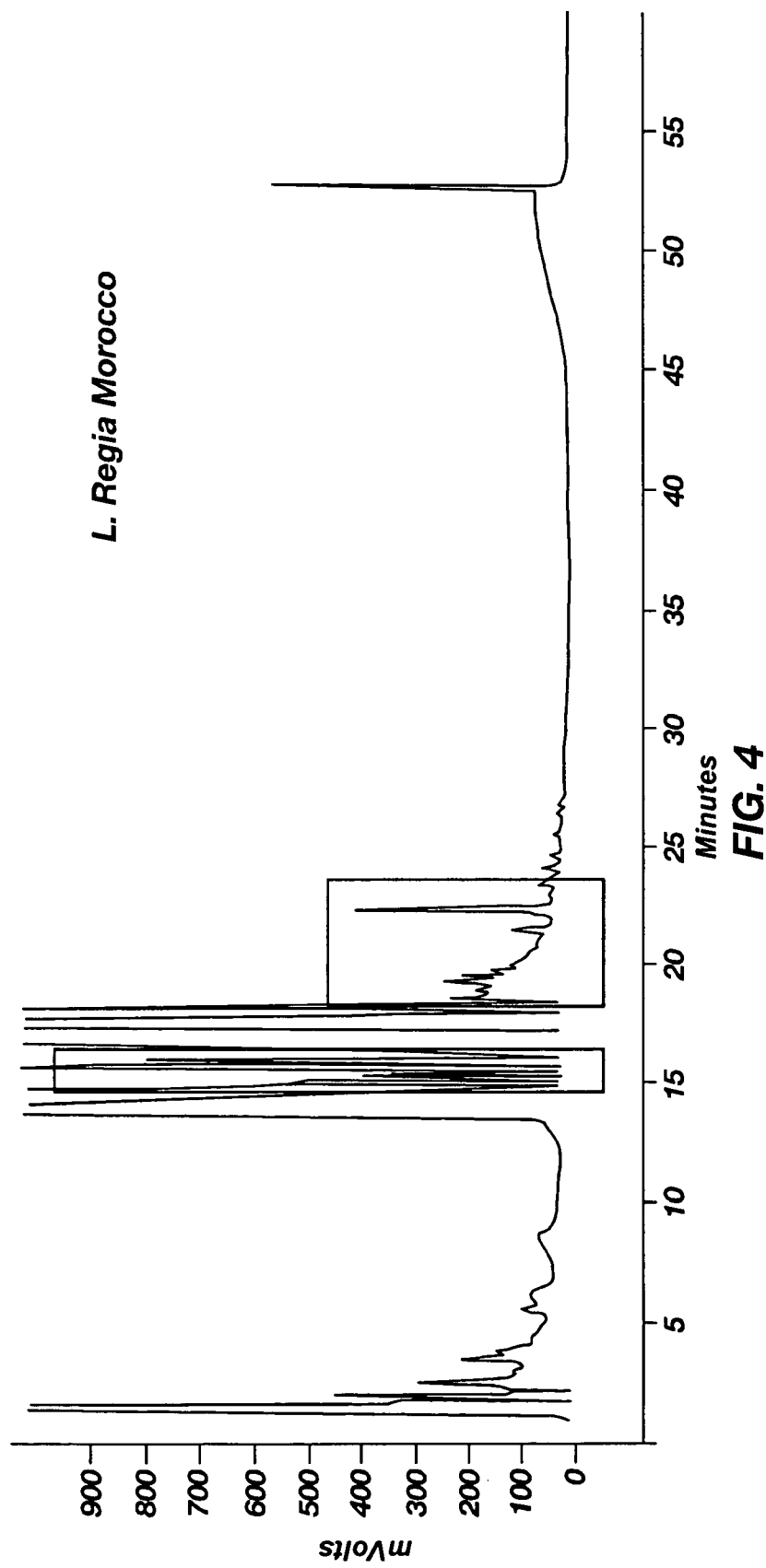
FIG. 4 depicts an HPLC tracing of a biologically active extract prepared in accordance with the present invention from the root of a Moroccan walnut tree.
Figure 5:
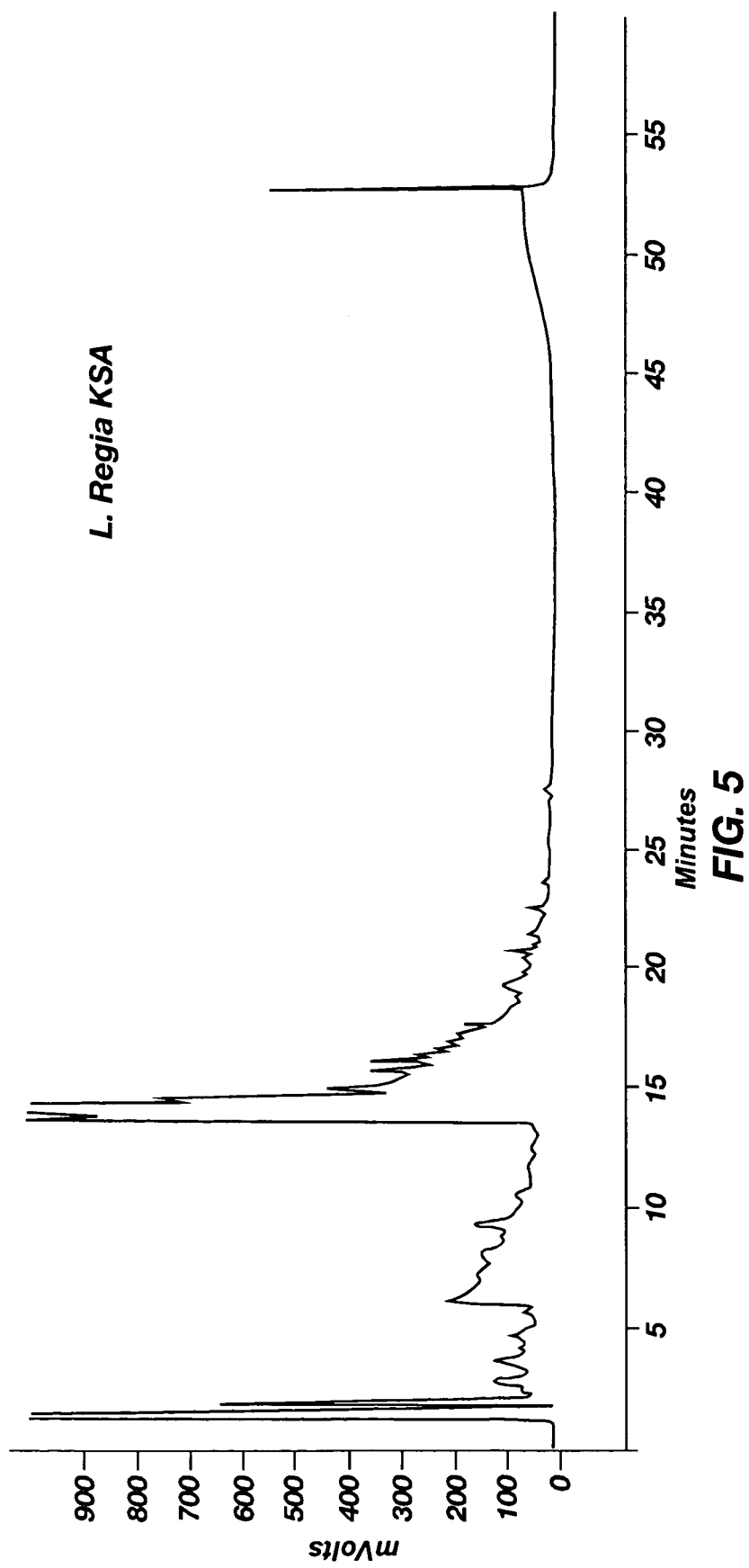
FIG. 5 depicts an HPLC tracing of an extract prepared from the root of a walnut tree grown in Saudi Arabia and belonging to the species *J. regia* L.

A comparison of the tracings of FIGS. 4 and 5 hereof shows that there is a difference in makeup of the biologically active extract of the present invention (FIG. 4) and an extract derived from a variety of walnut tree that is not within the scope of the present invention, that is, a walnut tree grown in Saudi Arabia. The extract which is the subject of the tracing of FIG. 4 is the Extract of Example No. 1 below. The extract of the tracing of FIG. 5 was prepared using the procedures of Example No. 1 below, except that the extract was derived from a walnut tree grown in Saudi Arabia, not the walnut tree grown in Morocco, which is the source of the biologically active extract of Example No. 1.

With respect to the HPLC tracings of FIGS. 4 and 5, the chromatography was performed using a C18 column (Vydac C18 (218TP54), 4.6×250 mm). The column was equilibrated with 0.1% TFA-Water(v/v) (Buffer A) and the concentrate was eluted with 0.1% TFA-60% acetonitrile-water (v/v) (Buffer B) at 1.2 mL/minute at a gradient of 0% B for 10 minutes, 0-100% B in 100 minutes. The elution was monitored by absorbance at 210 nm.

A comparison of the tracings of FIGS. 4 and 5 hereof shows that the chemical composition of the biologically active extract of the present invention is not that of the extract prepared from a walnut tree grown in Saudi Arabia. The HPLC peaks that correspond to the chemical composition of the anti-microbial fraction occur at a retention time between 26 and 30 minutes and are completely distinct from those of the extract from a walnut tree grown in Saudi Arabia; the HPLC peaks that correspond to extract from a walnut tree grown in Saudi Arabia occur at retention times of 0 to 25 and 31 to 38 minutes.

EXAMPLES

Examples which follow are illustrative of embodiments of the present invention. Comparative examples are set forth also.

Example No. 1

The following procedure was used to prepare a biologically active extract from the roots of a Moroccan walnut tree in accordance with the present invention.

A sufficient amount of the roots was dried by a commercial dryer and then crushed by a commercial grinder to form a number 10 powder. Twenty kg of the powder were added to 200 L of deionized water in a 600 L refrigerated vat equipped with a commercial mixer and the resulting mixture was stirred for 48 hours at 4° C. The mixture was then pressed using a commercial 40 mesh perforated presser to recover 150 L of a first liquid extract containing water-soluble ingredients from the root as the liquid extract was separated from the powder residue (hereinafter "step one"). Fifty L of water were added to the powder residue (about 180 kg) from the pressing of the first extract and the mixture was stirred for 48 hours at 4° C.

The mixture was then pressed as described above and added to the first extract (hereinafter "step two"). Fifty L of a second liquid extract were recovered. An additional 20 kg of root powder were then added to the 200 L of the first and second liquid extracts. The resulting mixture was stirred for 48 hours at 4° C. The mixture was then pressed to recover 150 L of a third liquid extract (hereinafter "step three"). Fifty L of water were added to the powder residue from the pressing of the third liquid extract and the resulting mixture was stirred for 48 hours at 4° C. The mixture was then pressed to recover 50 L of a fourth extract (hereinafter "step four").

The cycle comprising the third and fourth steps was repeated 48 times at which time a concentrated liquid solution (about 150 L) was obtained; it comprised about 20 g of the biologically active extract per 100 L of aqueous solution of extract (about 20 wt. %). The concentrated liquid solution was then strained through a serial filtration system using from 60-micron to 0.22-micron size filters to remove impurities and sterilize the extract.

The next example is illustrative of a mouthwash which is within the scope of the present invention and which is prepared from the biologically active extract of Example No. 1; thus, it includes the anti-microbial fraction of the present invention.

Example No. 2

The mouthwash of this example comprised the following ingredients.

|  | % Wt. |
|---|---|
| biologically active extract of Example No. 1 | 20.0 |
| thymol | 0.012 |
| menthol | 0.008 |
| sorbitol | 5.0 |
| PEG-40 | 0.15 |
| polysorbate 80 | 1.0 |
| ceteyl pyridium chloride | 0.2 |
| benzoic acid | 0.125 |
| fragrance | 2.5 |
| sodium saccharine | 0.002 |
| colorant | 0.002 |
| flavor | q.s |
| deionized water, balance | q.s |

The mouthwash of Example No. 2 was prepared by mixing initially all of the ingredients together, but for polysorbate 80 and PEG-40, which are the final ingredients added to the mixture.

The next example relates to the evaluation of the anti-microbial activity of the extract of the present invention against 13 strains of bacteria of the type that could be present throughout the body.

Example No. 3

This example involved the use of two biologically active extracts of the present invention. One of the extracts was prepared by the procedure involving only step one and step two as described in Example No. 1 hereof. This extract is described herein as "the 1× Extract." The other extract was prepared following steps one to four as described in Example No. 1, and then repeating step three and step four 13 times. This extract is described herein as "the 15× Extract." Accordingly, the concentration of the ingredients comprising the 15× Extract was substantially greater than the concentration of the ingredients comprising the 1× Extract.

Each strain of bacteria involved in the testing was cultured by incubating the strains on 75 mm agar plates with 200 µl of liquid broth. Twenty µl of 1× Extract were added to 6 mm blank paper disks (BBL) from Becton Dickinson & Co. and let dry. Four BBL 6 mm paper dried disks (Becton and Dickinson and Company) containing the 1× Extract were then placed in each of the bacteria-inoculated agar plates. Each strain of bacteria was incubated overnight at 37° C. in a VWR incubator model, after which the diameter of the zone of growth inhibition around the disks was measured. For each strain of bacteria, there was a control that involved the aforementioned culturing of the strains, but treatment of the extract was replaced with either 70% alcohol or liquid broth medium. The aforementioned procedure was repeated for the 15× Extract.

Table 1 below lists the diameter of the zone of growth inhibition around the disks for the 1× Extract and the 15× Extract, the diameter of the control culture, and the total percent inhibition of the bacterial culture by the 1× Extract and the 15× Extract. The total percent of inhibition was calculated by subtracting the zone of growth inhibition measurement from the control, dividing that number by the control, and then multiplying that number by 100.

TABLE 1

| Bacteria | Diameter (mm) 1× Extract | Diameter (mm) 15× Extract | Diameter (mm) Control | Inhibition % 1× Extract | Inhibition % 15× Extract |
|---|---|---|---|---|---|
| B. forsythus | 7.05 | 3.30 | 9.8 | 28.06 | 66.33 |
| E. Coli | 6.95 | 3.74 | 9.94 | 30.08 | 62.37 |
| Fusobacterium | 5.83 | 3.90 | 8.98 | 35.08 | 56.57 |
| Haemophilus | 5.65 | 4.29 | 9.27 | 39.05 | 53.72 |
| K. pneumoneae | 6.45 | 3.53 | 9.36 | 31.09 | 62.29 |
| P. aeruginosa | 6.74 | 3.66 | 9.64 | 30.08 | 62.033 |
| P. gingivalis | 6.77 | 3.86 | 9.96 | 32.03 | 61.24 |
| P. intermedia | 6.56 | 4.23 | 9.94 | 34.00 | 57.44 |
| S. aureus | 6.50 | 4.54 | 10.01 | 35.06 | 54.64 |
| S. pneumoneae | 6.02 | 3.62 | 8.99 | 33.04 | 59.73 |
| T. denticola | 6.44 | 3.47 | 9.21 | 30.08 | 62.32 |
| T. sokranskii | 6.37 | 4.09 | 9.52 | 33.09 | 57.04 |
| Veillonella | 6.43 | 3.24 | 9.17 | 29.88 | 64.67 |

Table 1 above shows that the 1× Extract and the 15× Extract had an inhibitory effect on each of the above-identified 13 strains of bacteria.

The next example illustrates the anti-fungal effect of the extract of the present invention.

Example No. 4

The following procedure was used to test the anti-fungal activity of a biologically active extract of the present invention against the fungus *Candida albicans*. The procedure involved the use of the Minimum Inhibitory Concentration (MIC) assay; it was used to determine the lowest concentration of the biologically active extract that will inhibit growth of the fungus. The assay was conducted according to the standard method described in the Manual of Clinical Microbiology, "Susceptibility Testing of Microdilution and Macrodilution Broth Procedures," Ch 101-102 (1985). The extract used in the MIC assay was the extract of Example No. 1 hereof. The tests showed that the extract was effective in inhibiting the growth of *Candida albicans*.

A MIC assay was also conducted to comparatively test a biologically active extract of the present invention and an extract prepared from walnut trees grown in America. Both of the extracts were prepared by the procedure involving only steps one to four as described in Example No. 1 hereof. The biologically active extract of the present invention prepared by steps one to four, and then repeating step three and step four 2 times, is described herein as "the 4× extract." The extract prepared by steps one to four, and then repeating step three and step four 2 times from walnut trees grown in America is described herein as "the American 4× extract."

Comparative tests of the 4× extract and the American 4× extract showed that the 4× extract of the present invention was effective in inhibiting the growth of *Candida albicans*, whereas the American 4× extract was unable to inhibit the growth of *Candida albicans*.

The following procedure was used to evaluate the anti-cancer activity of the biologically active extract of Example No. 1 against breast cancer cells.

Example No. 5

The evaluation involved the use of the biologically active extract of Example No. 1 in various water diluted forms to vary the concentration of the extract. The biologically active extract had a cytotoxic effect on the breast cancer cells at all concentrations tested.

A 96-well plate was plated with MCF-7 type breast adenocarcinoma cells at a concentration of $5 \times 10^4$/ml in culture media in an amount of 200 µl per well. The culture media comprised EME, 5% fetal bovine serum, 75 mM HEPES, 2 mM L-glutamine, 100 µg/ml of bovine pancreas insulin, 1 mM of penicillin, 1 mM of streptomycin, and 1 mM of sodium pyruvate. The cells were incubated for 24 hours at 37° C. in a carbon dioxide incubator set at 5%. The biologically active extract of Example No. 1 was diluted with water, as necessary, in amounts sufficient to provide the following dilutions 1/10, 1/15, 1/20, 1/40, 1/80, and 1/160. The dilutions of the biologically active extract were added to the breast cancer cells which were then incubated for 48 hours under the above-described conditions. Wells containing only culture medium and breast cancer cells, and wells containing only culture medium, breast cancer cells, and water were used as controls.

The culture medium was aspirated and the wells were washed once with 200 µl of DPBS, which was then removed. Two hundred µl of culture medium containing 0.863 mg/ml of MTT was added to each well. The cells were then further incubated for four hours under the above-described conditions, after which the culture medium was aspirated and solubilized in 200 µl of DMSO. Cell survival was determined by measuring the optical density of the cells in each well with a micro titer plate reader set at 560 nm. Table 2 below identifies the concentration of cancer cells remaining after treatment with each dilution of the biologically active extract of Example No. 1.

TABLE 2

| Extract Dilution/ Control Type | Test 1 (OD) | Test 2 (OD) | Mean test value (OD) | Background Noise | % Cytotoxicity (Mean value) |
| --- | --- | --- | --- | --- | --- |
| Blank | 0.045 | 0.048 | 0.047 | 0 | 0 |
| Water | 0.154 | 0.164 | 0.159 | 0.112 | 0 |
| Extract 1/10 dil. | 0.044 | 0.048 | 0.046 | −0.001 | 71.70 |
| Extract 1/15 dil. | 0.048 | 0.047 | 0.048 | 0.001 | 69.18 |
| Extract 1/20 dil. | 0.059 | 0.054 | 0.057 | 0.009 | 58.49 |
| Extract 1/40 dil. | 0.068 | 0.066 | 0.067 | 0.020 | 45.28 |
| Extract 1/80 dil. | 0.104 | 0.122 | 0.113 | 0.066 | −25.79 |
| Extract 1/160 dil. | 0.145 | 0.192 | 0.169 | 0.122 | −83.02 |

Table 2 shows that the 1/10, 1/15, 1/20, and 1/40 dilutions of the biologically active extract had a cytotoxic effect on breast cancer cells, and that the 1/80 and 1/160 dilutions of the biologically active extract did not have a cytotoxic effect on breast cancer cells.

What is claimed is:

1. A process for extracting an anti-microbial fraction from a root or bark of *Juglans regia* (*J. regia* L.) comprising treating the root or bark with an aqueous solvent for a sufficient period of time to extract from the root or bark an aqueous solution which contains in dissolved form a desired amount of a biologically active extract, wherein the aqueous solvent comprises at least about 70% water; separating by liquid chromatography an anti-microbial fraction from the biologically active extract; and recovering the anti-microbial fraction therefrom.

2. The process according to claim 1, wherein the aqueous solution contains at least about 20 wt. % of the biologically active extract.

3. The process according to claim 1, wherein the aqueous solvent comprises about 100 wt. % water.

4. The process according to claim 1, wherein the aqueous solvent comprises about 90 wt. % water.

5. The process according to claim 4, wherein the aqueous solvent comprises about 90 wt. % water and about 10 wt. % alcohol.

6. The process according to claim 5, wherein the alcohol is ethanol.

7. The process according to claim 1, wherein the aqueous solvent further comprises about 30 wt. % alcohol.

8. The process according to claim 7, wherein the alcohol is ethanol.

9. The process according to claim 1, wherein the aqueous solvent is at a solvent temperature of about 4° C. to about 20° C. and wherein the root or bark_is being treated with the aqueous solvent for a period of time sufficient to extract from the root or bark an aqueous solution which contains in dissolved form at least about 20 wt. % of the biologically active extract.

10. The process according to claim 9, wherein the solvent temperature is about 40° C. and the solution contains about 20 wt. % of the biologically active extract.

11. The process according to claim 1, wherein the root or bark is obtained from a Moroccan Walnut tree.

12. The process according to claim 1, wherein the root or bark is obtained from a tree selected from the group consisting of walnut trees grown in Morocco, Spain, Turkey, Afghanistan, Southern Russia, India, China, Greece, Chile, Iran, Japan, Tunisia, Algeria, France, Portugal, Southeast Asia, Bangladesh, Bahrain, Iraq, Israel, Jordan, Kuwait, Lebanon, Oman, Qatar, Syria, United Arab Emirates (UAE), Yemen, Cyprus, Armenia, Azerbaijan, Georgia, Libya, Egypt, Sudan, Mauritania, Mali, Niger, Nigeria, Chad, and Ethiopia, or such trees grown in other geographical areas.

\* \* \* \* \*

UNITED STATES PATENT AND TRADEMARK OFFICE
CERTIFICATE OF CORRECTION

| | |
|---|---|
| PATENT NO. | : 7,541,054 B2 |
| APPLICATION NO. | : 11/197909 |
| DATED | : June 2, 2009 |
| INVENTOR(S) | : Bassam B. Damaj |

It is certified that error appears in the above-identified patent and that said Letters Patent is hereby corrected as shown below:

In the specification:

COLUMN 4, LINE 36, change "aforementioned "solution I"" to --aforementioned "solution 1"--

In the claims:

CLAIM 10, COLUMN 13, LINE 13, change "40° C." to --4° C.--

Signed and Sealed this
Fifteenth Day of December, 2015

Michelle K. Lee
*Director of the United States Patent and Trademark Office*